(12) United States Patent
Zehner et al.

(10) Patent No.: US 6,410,785 B1
(45) Date of Patent: Jun. 25, 2002

(54) METHOD FOR PRODUCING ACROLEIN BY HETEROGENEOUS CATALYTIC GAS-PHASE PARTIAL OXIDATION OF PROPENE

(75) Inventors: Peter Zehner, Ludwigshafen; Otto Machhammer; Heiko Arnold, both of Mannheim; Klaus Joachim Müller-Engel, Stutensee, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/869,294

(22) PCT Filed: Jan. 15, 2000

(86) PCT No.: PCT/EP00/00304

§ 371 (c)(1), (2), (4) Date: Jul. 18, 2001

(87) PCT Pub. No.: WO00/43341

PCT Pub. Date: Jul. 27, 2000

(30) Foreign Application Priority Data

Jan. 22, 1999 (DE) .......................... 199 02 562

(51) Int. Cl.⁷ .......................... C07C 51/25; C07C 45/35
(52) U.S. Cl. .................. 562/532; 562/535; 562/546; 568/476; 568/477; 568/478; 568/479; 568/480
(58) Field of Search .................. 568/479, 480, 568/478, 476; 562/546, 532, 535

(56) References Cited

U.S. PATENT DOCUMENTS

| | | | |
|---|---|---|---|
| 3,198,750 A | 8/1965 | Callahan et al. | |
| 3,736,355 A | 5/1973 | Croci et al. | |
| 3,801,634 A | 4/1974 | Krabetz et al. | |
| 3,865,873 A | 2/1975 | Oda et al. | |
| 3,867,345 A | 2/1975 | Koberstein et al. | |
| 4,031,135 A | 6/1977 | Engelbach et al. | |
| 4,147,885 A | 4/1979 | Shimizu et al. | |
| 4,224,187 A | 9/1980 | Vanderspurt | |
| 4,837,360 A | * 6/1989 | Kadowaki et al. | 562/546 |
| 5,198,581 A | * 3/1993 | Kawajiri et al. | 562/546 |
| 5,684,188 A | * 11/1997 | Hefner et al. | 562/532 |
| 5,739,391 A | 4/1998 | Ruppel et al. | |
| 5,821,390 A | 10/1998 | Ruppel et al. | |
| 6,090,977 A | * 7/2000 | Hefner et al. | 562/512.2 |

FOREIGN PATENT DOCUMENTS

| | | |
|---|---|---|
| DE | 1 205 502 | 11/1965 |
| DE | 1 272 912 | 7/1968 |
| DE | 1 962 431 | 6/1970 |
| DE | 2 009 172 | 9/1971 |
| DE | 2 056 614 | 6/1972 |
| DE | 2 251 364 | 5/1973 |
| DE | 2 202 734 | 7/1973 |
| DE | 24 36 818 | 2/1976 |
| DE | 29 43 707 | 5/1980 |
| DE | 30 06 894 | 9/1980 |
| DE | 44 31 949 | 3/1995 |
| DE | 44 31 957 | 3/1995 |
| DE | 195 08 531 | 9/1996 |
| EP | 0 117 146 | 8/1984 |
| EP | 0 253 409 | 1/1988 |
| EP | 0 257 565 | 3/1988 |
| EP | 0 293 224 | 11/1988 |
| EP | 0 450 596 | 10/1991 |
| EP | 0 731 080 | 9/1996 |
| GB | 1 450 986 | 9/1976 |

* cited by examiner

*Primary Examiner*—Sreeni Padmanabhan
(74) *Attorney, Agent, or Firm*—Oblon, Spivak, McClelland, Maier & Neustadt, P.C.

(57) ABSTRACT

In a process for the preparation of acrolein by gas-phase partial oxidation under heterogeneous catalysis, a reaction gas starting mixture which contains propene and molecular oxygen in a molar $C_3H_6:O_2$ ratio of >1 is reacted in reaction zones connected in series, at elevated temperatures, over solid-state catalysts, further molecular oxygen being added to the reaction gas mixture in the course of the partial oxidation.

9 Claims, 1 Drawing Sheet

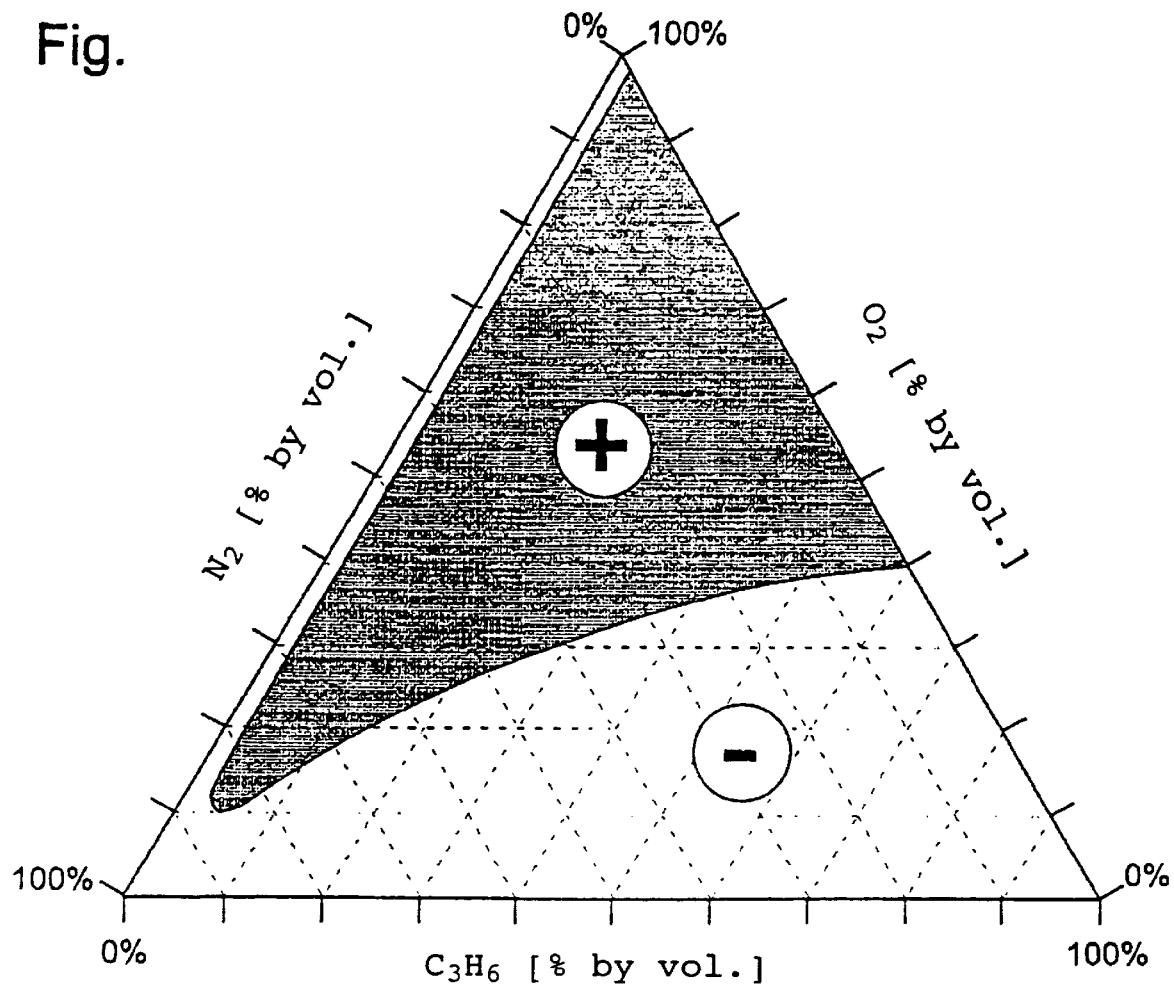

METHOD FOR PRODUCING ACROLEIN BY HETEROGENEOUS CATALYTIC GAS-PHASE PARTIAL OXIDATION OF PROPENE

This is U.S. National Stage Application of PCT/EP00/00304 filed Jan. 15, 2000, now WO 00/43341 published Jul. 27, 2000.

The present invention relates to a process for the preparation of acrolein by gas-phase partial oxidation of propene with molecular oxygen under heterogeneous catalysis over solid-state catalysts.

Acrolein is an important intermediate, for example for the preparation of glutardialdehyde, methionine, folic acid and acrylic acid.

It is generally known that acrolein can be prepared by a gas-phase oxidation of propene with molecular oxygen under heterogeneous catalysis over solid-state catalysts (cf. for example DE-A 1 962 431, DE-A 2 943 707, German patent 1 205 502, EP-A 257 565, EP-A 253 409, German published application 2 251 364, EP-A 117 146, British patent 1 450 986 and EP-A 293 224). The catalysts to be used are normally oxide materials which usually ensure high selectivity of the acrolein formation. The acrolein formation is frequently accompanied by a certain degree of acrylic acid formation, as one of the byproducts. Apart from oxygen, the catalytically active oxide material may contain only one other element or more than one other element (multi-element oxide materials). Particularly frequently used catalytically active oxide materials are those which comprise more than one metallic element, in particular transition metal element. In this case, the term multimetal oxide materials is used. Usually, the multimetal oxide materials are not simple physical mixtures of oxides of the elemental constituents but heterogeneous mixtures of complex polycompounds of these elements. As a rule, such multimetal oxide materials contain the elements Mo, Bi and Fe. The gas-phase oxidation of propene to acrolein under heterogeneous catalysis is generally effected at elevated temperatures (usually a few hundred ° C., typically from 200 to 450° C.).

Since the gas-phase oxidation of propene to acrolein under heterogeneous catalysis is highly exothermic, it is expediently carried out in a fluidized bed or in multi-catalyst-tube fixed-bed reactors, through whose space surrounding the catalyst tubes a heat-exchange medium is passed. The latter procedure is the preferred one (cf. for example DE-A 4 431 957 and DE-A 4 431 949). The operating pressure (absolute pressure) is usually from 1 to 10 bar. The desired reaction takes place during the residence time of the reaction gas mixture in the catalyst load through which it is passed.

Owing to the extremely exothermic character of the partial oxidation of propene, the oxidation reactors are usually loaded with a mixture which contains the reactants molecular oxygen and propylene diluted with a gas which is essentially inert under the conditions of the gas-phase catalytic partial oxidation. This is understood here as meaning diluent gases whose components, each considered by itself, remain unchanged to an extent of more than 95, preferably more than 98, mol % under the conditions of the gas-phase partial oxidation under heterogeneous catalysis. Usually, the inert diluent gas accounts for the largest volume fraction of the three components of the loading gas. One object of the inert diluent gas is to absorb and remove heat evolved during the partial oxidation. The second object of the inert diluent gas is to reduce the tendency of the reaction mixture to explode. According to DIN 51 649, a gas mixture containing molecular oxygen and a flammable gas, such as propylene, is outside the explosion range under predetermined boundary conditions (pressure, temperature) when combustion (ignition, explosion) initiated by a localized ignition source (for example a glowing platinum wire) is no longer capable of propagating from the ignition source in the gas mixture.

The traditional processes of the gas-phase oxidation of propene to acrolein under heterogeneous catalysis recommend steam and/or nitrogen as inert diluent gas (cf. for example U.S. Pat. No. 4,147,885, DE-A 2 056 614, DE-A 52 009 172, DE-A 2 202 734, DE-A 3 006 894 and DE-A 2 436 818). The advantage of the presence of nitrogen as inert diluent gas is that it makes it possible to use air as a source of the molecular oxygen required in the partial oxidation of propene.

EP-A 293 224 recommends using, as inert diluent gas, a gas mixture consisting of carbon dioxide, steam and saturated hydrocarbons of 1 to 5 carbon atoms.

EP-A 253 409 states that inert diluent gases which have a high molar specific heat are advantageous. DE-A 19 508 531 states that inert diluent gases which have the property of flammability in addition to a high molar specific heat are particularly suitable inert diluent gases. In all the above-mentioned cases, the prior art furthermore recommends choosing the ratio of molecular oxygen to propene in the reaction gas starting mixture for the catalytic partial oxidation of propene to be $\geq 1$ and adding the total amount of molecular oxygen required for the catalytic partial oxidation of propene completely to the reaction gas starting mixture.

The disadvantage of the prior art procedure is that the inert diluent gases to be used are without exception valuable substances which, for cost reasons and being components of the product gas mixture, are usually separated from the desired product and are usually re-used as inert diluent gas by circulation (cf. for example EP-A 253 409) (this also applies when nitrogen alone is used as inert diluent gas since nitrogen introduced as an oxygen impurity when air is used as the oxygen source would not be sufficient in its amount as the sole diluent gas for a safe procedure, i.e. for safety reasons an additional nitrogen source (as a rule recycle nitrogen gas) is always required). However, the abovementioned circulation is expensive (where the product gas mixture of the partial oxidation of propene to acrolein is directly re-used for a subsequent partial oxidation of the acrolein present therein to acrylic acid, separation of the recycle gas is usually effected only after the acrylic acid stage with recycling to the acrolein stage).

It is an object of the present invention to provide a process for the preparation of acrolein by gas-phase partial oxidation of propene with molecular oxygen under heterogeneous catalysis over solid-state catalysts, which process has the described disadvantages of the prior art processes either only in reduced form or not at all.

We have found that this object is achieved by a process for the preparation of acrolein by gas-phase partial oxidation of propene with molecular oxygen under heterogeneous catalysis over solid-state catalysts, wherein a reaction gas starting mixture which contains propene and molecular oxygen in a $C_3H_6:O_2$ ratio of >1 is first passed, at elevated temperatures, through a first reaction zone I equipped with a first solid-state catalyst load I and a portion of the propene contained in the reaction gas starting mixture is oxidized to acrolein and then, to complete the partial oxidation of the propene to acrolein, the product gas mixture I emerging from the reaction zone I is passed, at elevated temperatures, through at least one further reaction zone having a solid catalyst load and, in at least one of the one or more further reaction zones, the molar ratio, present in the reaction gas mixture, of molecular oxygen to propene is increased by metering in molecular oxygen and/or a gas containing molecular oxygen, with the proviso that, in the product gas mixture emerging from the last reaction zone, at least 90 mol %, based on the propene fed to the reaction zone I, of the propene are converted with a selectivity of the acrolein formation of $\geq 80$ mol %.

The advantage of the novel process over the prior art processes is that the reaction mixture in every reaction zone contains a higher molar sum, based on the molar amount of molecular oxygen present, of propene and acrolein, which, in the same way as the inert diluent gas, reduces the tendency of the reaction gas mixture to explode and is capable of absorbing and removing heat evolved in the partial oxidation. Since both propene and acrolein furthermore have a high molar specific heat and the property of flammability, their abovementioned effect is very particularly pronounced, which permits a significant reduction in the amount of inert diluent gas to be added without impairing the safety. On the other hand, the propene, on passing through the reaction zones, is substantially converted into acrolein and is separated as such and as desired product from the product gas mixture leaving the final reaction zone and is not recycled as recycle gas, which is why the advantage of the novel procedure is to be regarded primarily as the fact that the amount of the inert gas to be circulated is reduced. When nitrogen is used as the sole inert diluent gas, circulation of the nitrogen may under favorable circumstances even be completely absent in the novel procedure since the amount of nitrogen contained in air as the oxygen source is sufficient as inert diluent gas. This is also true when the product gas mixture leaving the final reaction zone of the novel process is fed directly to an acrolein partial oxidation to acrylic acid under heterogeneous catalysis and the isolation of the desired product is not carried out until after the acrylic acid stage.

The advantage, described above, of the novel process is of course all the more pronounced the larger the number of reaction zones used into which molecular oxygen or a gas containing molecular oxygen is metered, i.e. the lower the chosen proportion of molecular oxygen in the reaction gas mixture inside a reaction zone. For reasons of expediency, the number of reaction zones into which molecular oxygen or a gas containing molecular oxygen is metered in the novel process will as a rule be not more than three; preferably, the novel process comprises two reaction zones, including the first reaction zone. The novel process advantageously comprises no further reaction zones into which both no molecular oxygen and no gas containing molecular oxygen is metered. If the molecular oxygen is metered in as a component of a gas mixture, for example in the form of air, the remaining components of the gas mixture are usually inert gases with respect to the novel process.

All those inert or diluent gases which are known from the prior art may be used as inert or diluent gases for the novel process. These are, for example, $N_2$, CO, $CO_2$, $H_2O$, saturated hydrocarbons (in particular $C_1$- to $C_5$-alkanes) and/or noble gases.

In the novel process, the various reaction zones may be loaded with one and the same catalyst or with catalysts differing from one another. What is essential according to the invention is merely that the catalyst load ensures sufficient selectivity of the acrolein formation. This is the case with numerous catalysts of the prior art. Suitable catalysts of this type are, for example, those of DE-A 2 909 592, especially those from Example 1 of said publication. Alternatively, however, multimetal oxide catalysts II and II' of DE-A 19 753 817 may also be used. This applies in particular to the exemplary embodiments mentioned in these publications, especially when they are in the form of unsupported hollow cylindrical catalysts as described in EP-A 575 897. It is of course also possible to use the Bi-, Mo- and Fe-containing multimetal oxide catalyst ACF-2 of Nippon Shokubai. The catalyst load of an-individual reaction zone may consist of a single catalyst, of a mixture of catalysts or of an arrangement of different catalysts in series. The reaction temperature in the reaction zones of the novel process is expediently chosen to be from 300 to 450° C., preferably from 320 to 390° C.

Of course, the reaction temperature may be the same or different in all reaction zones. As a rule, it is advantageous if the reaction temperatures increase in the direction of increasing propene conversion within the reaction zone.

The at least two reaction zones required according to the invention may be in the form of a fluidized bed and/or in the form of a fixed bed. According to the invention, they may furthermore be realized in a single reactor or in separate reactors connected in series. Preferably, the novel process is carried out in multi-catalyst-tube fixed-bed reactors. The two-zone multi-catalyst-tube fixed-bed reactor described in U.S. Pat. No. 4,203,906 is suitable, for example, for carrying out the novel process in a single reactor if, on transfer of the reaction gas to the second reaction zone, the possibility of metering in molecular oxygen or a gas containing molecular oxygen is provided. In both reaction zones, the reaction gas mixture and the heat-exchange medium can be fed cocurrent and/or countercurrent, considered over the individual reaction zone. The flow of the heat-exchange medium may be in the form of a pure longitudinal flow, in the form of longitudinal flow with superposed transverse flow or in the form of radial flow, as described in DE-A 2 201 528.

As a rule, an individual reaction zone within the novel process is however in the form of a self-contained multi-catalyst-tube fixed-bed reactor. The latter can, for example, be designed and operated as described in EP-A 700 714.

However, the countercurrent procedure described in EP-A 700 714 is of course also possible. What is essential according to the invention is that, on realizing the individual reaction zone as a multi-catalyst-tube fixed-bed reactor, in contrast to the parallel reactor connection suggested in "Encyclopedia of Chemical Processing and Design, Marcel Dekker, Inc., Vol. 1, Abrasives to Acrylonitrile, 1976, pages 410 to 412" a series connection of reactors results, underlining the difference between the novel procedure and the procedure of the prior art.

If the novel process is realized as a two-zone process, it is expedient in this context to connect two multi-catalyst-tube fixed-bed reactors in series and to operate both by the meander-like cocurrent procedure described in EP-A 700 714.

For example, the reaction gas starting mixture fed to the first reaction zone may have a propene:oxygen:essentially inert gas volume (1 (S.T.P.)) ratio of (>1.0 to 3.0):1:(10 to 1.5), preferably of (1.1 to 2.0):1:(10 to 1.5), particularly preferably of (1.2 to 1.5):1:(10 to 1.5). This is the case in particular when the novel process is designed as a two-zone process. The reaction pressure is usually from 0.5 to 5, particularly from 1 to 3, bar. The total space velocity when the novel process is carried out in a multi-catalyst-tube fixed bed is frequently from 1500 to 2500 l (S.T.P.)/l/h.

Whereas, in the novel process, the molar ratio of propene to molecular oxygen must be >1 in the reaction gas starting mixture fed to the first reaction zone (as a rule it is $\leq 3$), it is preferred according to the invention to carry out the metering of molecular oxygen into the downstream reaction zones in such a way that the molar ratio of molecular oxygen to propene is >1 at least in the reaction gas mixture fed to the final reaction zone. According to the invention, it is furthermore advantageous if the molar ratio of (propene and acrolein) to molecular oxygen in the reaction gas mixture of every reaction zone is >1.

Preferably, in the novel process, at least 95 mol %, based on the propene fed to the reaction zone I, of the propene are converted with a selectivity of the acrolein formation of ≧85 mol % in the product gas mixture emerging from the final reaction zone. Furthermore, the required molecular oxygen is preferably added in the form of air both to the reaction gas starting mixture and to the further reaction zones.

If, in the novel process, two multicatalyst fixed-bed reactors are connected in series, the molar ratio of propene to oxygen in the reaction gas starting mixture may be, for example, (>1.0 to 3.0):1, frequently (1.1 to 2.0):1 and that in the reaction gas mixture fed to the second multi-catalyst-tube fixed-bed reactor, after metering in of molecular oxygen, may be, for example, 1:(≧1.0 to 3.0), frequently 1:(1.5 to 2.0). Furthermore, the propene conversion in the first multi-catalyst-tube fixed-bed reactor is expediently from 20 to 60, frequently from 40 to 60, mol %, based on the propene fed in. The abovementioned applies generally in the case of a two-zone implementation. Particularly in the two-zone implementation of the novel process, it is useful to add the total amount of molecular oxygen required in the form of air and the nitrogen contained therein as the sole diluent gas. In this case gas circulation can usually be entirely dispensed with or limited to recycling of unconverted propene.

Of course, the novel process doesn't give pure acrolein but a gas mixture from which the acrolein can be isolated in a manner known per se (for example by absorption in an aqueous medium with subsequent separation by rectification). The acrolein isolated in this manner can be used as an intermediate for the synthesis of various end products. However, it can also be used in a gas-phase partial oxidation of acrolein with molecular oxygen under heterogeneous catalysis over solid-state catalysts for the preparation of acrylic acid. In such a further use of the acrolein for the preparation of acrylic acid in at least one further gas-phase catalytic oxidation zone, the acrolein-containing reaction gases of the final propene oxidation zone are usually transferred to these one or more further oxidation zones without removal of secondary components. If necessary, they are cooled beforehand.

This further gas-phase partial oxidation of acrolein to acrylic acid under heterogeneous catalysis can in principle be carried out completely analogously to the novel propene partial oxidation in a plurality of reaction zones connected in series. However, it can also be carried out in a manner known per se in a single reaction zone or in a plurality of reaction zones connected parallel to one another.

The reaction zones are expediently likewise realized as separate multi-catalyst-tube fixed-bed reactors, as described, for example, in EP-A 700 893 and in the prior art cited therein or in DE-A 4 431 949, DE-A 4 442 346, DE-A 19 736 105 or EP-A 731 082. Multimetal oxides suitable as catalysts in this context are, for example, those which contain the elements Mo and V. The reaction temperature in the reaction zone is expediently chosen to be from 200 to 300° C. preferably from 220 to 290° C.

The reaction pressure in the reaction zones is usually from 0.5 to 5, preferably from 1 to 3, bar. The total space velocity of the multi-catalyst-tube fixed-bed reactors is as a rule from 1000 to 2500 l (S.T.P.)/l/h. Suitable catalysts for the partial oxidation of acrolein to acrylic acid are, for example, those of the formulae I and I' from DE-A 4 442 346.

Alternatively, however, it is also possible to use the multimetal oxide catalysts of DE-A 19736105, in particular the embodiments stated in the abovementioned publication. The multimetal oxide catalyst ACS-4 from Nippon Shokubai, comprising Bi, Mo and Fe, can of course also be used in the acrolein oxidation stage. Where the reaction zones for the partial oxidation of acrolein are connected in series, the statements relating to the novel propene partial oxidation in other respects are applicable in a corresponding manner.

Where the reaction zones are connected in parallel or there is a limitation to a single reaction zone, as a rule an acrolein:oxygen:steam:other essentially inert gas volume (1 (S.T.P.)) ratio of 1:(0.90 to 3):(>0 to 20):(3 to 30), preferably of 1:(0.90 to 3):(0.5 to 10):(7 to 18) is employed in the reaction gas feed mixture. To achieve the desired ratios, it is usually necessary additionally to introduce molecular oxygen into the acrolein-containing product gas mixture from the final propene oxidation zone before it is passed into the one or more acrolein oxidation zones. This can be effected by means of air, by means of nitrogen-depleted air or by means of pure oxygen. Additional diluent gases essentially known to be inert can of course be added as desired at this point.

The gas mixture leaving the final acrolein oxidation zone does not of course consist of pure acrylic acid but of a gas mixture which contains the latter and from which acrylic acid can be isolated in a manner known per se.

The various known methods of acrylic acid isolation are summarized, for example, in DE-A 19 600 955. In a corresponding manner, the acrolein could also be isolated from the reaction gas mixture leaving the final propene oxidation zone. The common feature of the separation methods is that the desired product is isolated from the product gas mixture either by absorption with a solvent (cf. also DE-4308087) or by absorption with water and/or by partial condensation. The resulting absorbate or condensate is then worked up by distillation (with or without the addition of an azeotropic entraining agent) and/or by crystallization, and essentially pure acrylic acid or pure acrolein is thus obtained. The separation line in all cases is essentially drawn so as to give a residual gas stream which is essentially free of acrylic acid and/or acrolein and whose main component comprises the inert diluent gases and which can be partly or wholly re-used as an inert diluent gas by gas circulation.

However, the advantage of the novel process is that it minimizes the amount of circulated inert diluent gas used. Particularly important according to the invention is the fact that this is possible without reducing the space-time yield. The novel process also makes use of the fact that $H_2O$ is formed as a by-product of the relevant catalytic gas-phase oxidation and acts as an additional inert diluent gas along the reaction path.

Finally, it may be noted that the novel process can of course be applied in a fully corresponding manner to the gas-phase partial oxidation of isobutyric acid, tert-butanol, isobutene, isobutyraldehyde and/or the methyl ether of tert-butanol under heterogeneous catalysis to give methacrolein and/or methacrylic acid.

EXAMPLES

Preparation of acrolein and acrylic acid by gas-phase partial oxidation of propene with molecular oxygen under heterogeneous catalysis over solid-state catalysts (in the analysis given below, the small amount of noble gases contained in air is included in the nitrogen fraction of the air)

A) Series Connection According to the Invention 14.0 mol/h of industrial propene (this is a mixture of propene and propane with a propane content of 4.3% by volume) and 52.4 mol/h of air are combined to give 66.4 mol/h of reaction gas starting mixture composed of

- 20.19% by volume of propene,
- 60.96% by volume of $N_2$,
- 16.15% by volume of $O_2$,
- 1.77% by volume of $H_2O$,
- 0.03% by volume of $CO_2$, and
- 0.9% by volume of other components, compressed to 1.90 bar and heated to 200° C. A first reaction tube (V2A stainless steel; length 3.80 m; 2.0 mm wall thickness; 2.6 cm internal diameter) which is cooled over its entire length to 340° C. by means of a salt bath is loaded, as the first propene oxidation zone, with the abovementioned reaction gas starting mixture. In the direction of flow, the reaction tube is loaded over a length of 50 cm with a preliminary bed of steatite beads (diameter: 4–5 mm). This is followed over a catalyst tube length of 3.00 m by a bed of multimetal oxide catalyst according to Example 1, 3./multimetal oxide II from DE-A 19753817. The product gas mixture leaving the first reaction tube in an amount of 66.5 mol/h is immediately cooled indirectly to 200° C. to avoid undesired subsequent combustion and has the following composition:

- 10.07% by volume of propene,
- 9.11% by volume of acrolein,
- 0.50% by volume of acrylic acid,
- 60.79% by volume of $N_2$,
- 4.50% by volume of $O_2$,
- 12.74% by volume of $H_2O$,
- 0.60% by volume of CO,
- 0.78% by volume of $CO_2$ and
- 0.91% by volume of other components.

36.3 mol/h of air are mixed with said product gas mixture and the resulting 102.8 mol/h of reaction gas mixture composed of

- 6.51% by volume of propene,
- 5.89% by volume of acrolein,
- 0.33% by volume of acrylic acid,
- 66.61% by volume of $N_2$,
- 10.14% by volume of $O_2$,
- 9.03% by volume of $H_2O$,
- 0.39% by volume of CO,
- 0.52% by volume of $CO_2$ and
- 0.58% by volume of other components are fed, at an inlet pressure of 1.75 bar and an inlet temperature of 200° C., to a second reaction tube (V2A stainless steel; length 3.80 m; 2.0 mm wall thickness; 2.6 cm internal diameter) which acts as a second propene oxidation zone and is cooled over its entire length to 350° C. by means of a salt bath. In the direction of flow, the second reaction tube is loaded over a length of 50 cm with a preliminary bed of steatite beads (diameter: 4–5 mm). This is followed over a catalyst tube length of 3.00 m by a bed of the multimetal oxide catalyst according to Example 1,3./multimetal oxide II from DE-A 19753817. The product gas mixture leaving the second reaction tube in an amount of 103.0 mol/h is immediately cooled indirectly to 200° C. to avoid undesired subsequent combustion and has the following composition:

- 0.33% by volume of propene,
- 11.47% by volume of acrolein,
- 0.63% by volume of acrylic acid,
- 66.49% by volume of $N_2$,
- 3.0% by volume of $O_2$,
- 15.75% by volume of $H_2O$,
- 0.76% by volume of CO,
- 0.98% by volume of $CO_2$ and
- 0.59% by volume of other components.

40.0 mol/h of air are mixed with said product gas mixture to give 143.0 mol/h of a reaction gas mixture having the following composition:

- 0.23% by volume of propene,
- 8.27% by volume of acrolein,
- 0.46% by volume of acrylic acid,
- 69.51% by volume of $N_2$,
- 7.88% by volume of $O_2$,
- 11.97% by volume of $H_2O$,
- 0.55% by volume of CO,
- 0.71% by volume of $CO_2$ and
- 0.42% by volume of other components.

The abovementioned reaction gas mixture is divided into two part-streams of equal magnitude which are used for loading two reaction tubes connected in parallel as acrolein oxidation zones (inlet pressure=1.45 bar, inlet temperature= 200° C.). These reaction tubes (V2A stainless steel; length: 3.80 m, 2.0 mm wall thickness; 2.6 cm internal diameter) are each loaded, in the direction of flow, first with a preliminary bed of steatite beads (diameter: 4–5 mm) over a length of 50 cm. This is followed over a catalyst tube length of 2.70 m by a bed of the multimetal oxide catalyst according to Example b, S1 of DE-A 4442346. The reaction tubes are kept at 270° C. over their entire length by means of a salt bath. The outlet pressure of the reaction tubes is 1.35 bar. The product gas mixtures leaving the two reaction tubes connected in parallel are combined to give 137.6 mol/h of a total product gas mixture having the following composition:

- 0.24% by volume of propene,
- 0.04% by volume of acrolein,
- 8.55% by volume of acrylic acid,
- 72.24% by volume of $N_2$,
- 3.15% by volume of $O_2$,
- 12.87% by volume of $H_2O$,
- 0.83% by volume of CO,
- 1.38% by volume of $CO_2$ and
- 0.7% by volume of other components.

The hot total product gas mixture leaving the acrolein oxidation stage is cooled to about 160° C. in a Venturi scrubber (quench apparatus) by direct contact with quench liquid (140–150° C.) to be sprayed in through slots mounted in the region of the narrowest cross-section of the Venturi tube and comprising 57.4% by weight of diphenyl ether, 20.7% by weight of biphenyl and 20% by weight of o-dimethyl phthalate. Then that proportion of the quench liquid which has remained in the form of liquid droplets is separated from the gas phase consisting of reaction gas and vaporized quench liquid in a downstream mist separator (receiver with gas tube leading upward) and recycled in a circulation I to the Venturi scrubber. A part-stream of the recycled quench liquid is subjected to solvent distillation, the quench liquid distilling over and high-boiling secondary components remaining behind and being incinerated. The quench liquid which has distilled over is fed to the discharge of the absorption column described below.

The gas phase at about 160° C. is fed to the lower part of a packed absorption column (3 m high; double jacket of glass; internal diameter 50 mm; packing zones (from bottom to top) 90 cm, 90 cm and 50 cm long; the packing zones are thermostatted as follows from bottom to top: 90° C., 60° C., 20° C.; the penultimate and final packing zones are separated by a chimney tray; the packings are stainless steel coils having a coil diameter of 5 mm and a pitch of 5 mm; the absorbent is fed in directly above the middle packing zone) and it is exposed to the countercurrent of 4900 g/h of the absorbents which are likewise composed of 57.4% by weight of diphenyl ether, 20.7% by weight of biphenyl and 20% by weight of o-dimethyl phthalate and are added at a temperature of 50° C. The discharge of the absorption column, which, in addition to acrylic acid, also contains low-boiling by-products, such as acrolein and acetic acid, in absorbed form, is heated indirectly to 100° C. in a heat exchanger and fed to the top of a desorption column, which is likewise in the form of a packed column having a length of 2 m (double jacket of glass; 50 mm internal diameter; packings: stainless steel coils having a coil diameter of 5 mm and a pitch of 5 mm; one packing zone 1 m long; thermostatted at 120° C.). In the desorption column, the components having a lower boiling point than acrylic acid, such as acrolein and acetic acid, are substantially removed from the acrylic acid/absorbent mixture by stripping with a residual gas leaving the absorption column (22.8 mol/h of residual gas; countercurrent; feed temperature 120° C.). The laden stripping gas leaving the desorption column is recirculated and is combined with the hot reaction gas of the acrolein oxidation stage before its entry into the Venturi quench.

The unabsorbed gas mixture leaving the second packing zone in an upward direction in the absorption column is further cooled in the third packing zone to separate off the readily condensable part of all the secondary components contained therein, for example water and acetic acid, by condensation. This condensate is referred to as dilute acid solution. To increase the separation efficiency, a part of the dilute acid solution is recycled to the absorption column at a temperature of 20° C., above the third packing zone of the absorption column. The dilute acid solution is removed below the uppermost packing zone, from the chimney tray mounted there. The reflux ratio is 200. The amount of dilute acid solution to be removed continuously is 15.6 mol/h. In addition to 90.3% by weight of water, it contains 2.60% by weight of acrylic acid. This can, if required, be recovered as described in DE-A 19600955. The residual gas finally leaving the absorption column is partly used for stripping and otherwise forms waste gas.

The bottom liquid of the desorption column is fed to the $8^{th}$ tray from below of a tray column containing 57 dual-flow trays (internal diameter: 50 mm; length: 3.8 m; top pressure: 100 mbar; bottom pressure: 280 mbar; bottom temperature: 195° C.; a pressure drop resistance is mounted at the $9^{th}$ tray) and is rectified therein. 11.7 mol/h of crude acrylic acid are removed per hour from the $48^{th}$ tray from the bottom, via a side take-off. The purity of the crude acrylic acid is 99.5% by weight. An acrylic acid-containing gas stream enriched with slow boilers is taken off at the top of the rectification column after a partial condensation and, after its complete condensation in a cold trap (32 g/h), is recycled to the absorption column, above the lowermost packing zone. The absorbent free of low boilers and virtually free of acrylic acid is taken off from the bottom of the rectification column and recycled to the absorption column, above the second packing zone (considered from below). Phenothiazine, as a polymerization inhibitor, is added to the reflux at the top of the rectification column, in an amount such that the side take-off contains 300 ppm of phenothiazine (a schematic diagram of the working-up process for the reaction gas of the acrolein oxidation stage is shown in DE-A 19600955; in addition, the working-up procedure is also described in DE-A 4308087). The residual gas leaving the absorption column is composed of 0.30% by volume of propene,
0.02% by volume of acrolein,
0% by volume of acrylic acid,
90.08% by volume of $N_2$,
3.93% by volume of $O_2$,
2.36% by volume of $H_2O$,
1.03% by volume of CO,
1.72% by volume of $CO_2$ and
0.557% by volume of other components.

The amount of the residual gas stream is 110.3 mol/h.

BRIEF DESCRIPTION OF THE DRAWINGS

The FIGURE is a graphic representation of the gas phase oxidation propene.

As shown in the FIGURE attached to this application, the gas-phase partial oxidation is from the outset safely outside the explosion range (the figure shows the separation line of "in the explosion range" [⊕] and "outside the explosion range" [⊖] in the ternary nitrogen ($N_2$)-propene($C_3H_6$)-oxygen ($O_2$)-diagram under the boundary condition of 180° C. and 1 bar). Gas circulation can be completely dispensed with.

B) Traditional Parallel Connection 14.0 mol/h of industrial propene, 107.3 mol/h of air and 140.5 mol/h of recycle gas composed of 0.28% by volume of propene,
0.02% by volume of acrolein,
0% by volume of acrylic acid,
90.45% by volume of $N_2$,
3.50% by volume of $O_2$,
2.36% by volume of $H_2O$,
1.06% by volume of CO,
1.77% by volume of $CO_2$ and
0.56% by volume of other components
are combined to give 261.8 mol/h of reaction gas starting mixture composed of 5.26% by volume of propene,
0.01% by volume of acrolein,
0% by volume of acrylic acid,
80.21% by volume of $N_2$,
10.27% by volume of $O_2$,
2.19% by volume of $H_2O$,
0.57% by volume of CO,
0.96% by volume of $CO_2$ and
0.53% by volume of other components,
compressed to 1.90 bar and heated to 200° C.

The abovementioned reaction mixture is divided into two part-streams of the same magnitude which are used for loading two reaction tubes (V2A stainless steel; length 3.80 m; 2.0 mm wall thickness; 2.6 cm internal diameter) connected in parallel as propene oxidation zones. These reaction tubes, like the propene oxidation tubes in Example A), are each loaded over a length of 50 cm with a preliminary bed of steatite beads (diameter: 4–5 mm). This is followed over a catalyst tube length of 3.00 m by a bed of multimetal oxide catalyst according to Example 1, 3./multimetal oxide II from DE-A 19753817. Both reaction tubes are cooled to 350° C. over their entire length by means of a salt bath. The product gas streams leaving the reaction tubes are combined to give a total product gas stream of 262.1 mol/h having the following composition:

- 0.26% by volume of propene,
- 4.52% by volume of acrolein,
- 0.25% by volume of acrylic acid,
- 80.10% by volume of $N_2$,
- 4.5% by volume of $O_2$,
- 7.62% by volume of $H_2O$,
- 0.87% by volume of CO,
- 1.34 % by volume of $CO_2$ and
- 0.54% by volume of other components.

18.8 mol/h of air are mixed with the total product gas stream so that 280.9 mol/h of a reaction gas mixture having the following composition form:

- 0.25% by volume of propene,
- 4.22% by volume of acrolein,
- 0.23% by volume of acrylic acid,
- 79.91% by volume of $N_2$,
- 5.57% by volume of $O_2$,
- 7.26% by volume of $H_2O$,
- 0.81% by volume of CO,
- 1.25% by volume of $CO_2$ and
- 0.5% by volume of other components.

This reaction gas mixture is divided into two part-streams of the same magnitude which, at an inlet pressure of 1.55 bar and an inlet temperature of 200° C., are used for loading two reaction tubes (V2A stainless steel; length: 3.80 m; 2.0 mm wall thickness; 2.6 cm internal diameter) connected in parallel as acrolein oxidation zones. These reaction tubes, like the acrolein oxidation tubes in Example A), are each loaded over a length of 50 cm with a preliminary bed of steatite beads (diameter: 4–5 mm). This is followed over a catalyst tube length of 3.00 m by a bed of the multimetal oxide catalyst according to Example b, S1 of DE-A 4442346. Both reaction tubes are cooled to a temperature of 270° C. over their entire length by means of a salt bath. The product gas streams leaving the reaction tubes are immediately cooled indirectly to 200° C. to avoid undesired subsequent combustion and are combined to give a total product gas stream of 275.4 mol/h having the following composition:

- 0.25% by volume of propene,
- 0.02% by volume of acrolein,
- 4.29% by volume of acrylic acid,
- 81.49% by volume of $N_2$,
- 3.15% by volume of $O_2$,
- 7.62% by volume of $H_2O$,
- 0.95% by volume of CO,
- 1.59% by volume of $CO_2$ and
- 0.64% by volume of other components.

The hot total product gas stream leaving the acrolein oxidation stage is worked up in a manner corresponding to that in Example A). The following are obtained:

- 15.8 mol/h of dilute acid solution containing 82.8% by weight of water and 2.60% by weight of acrylic acid and
- 11.7 mol/h of 99.5% strength by weight of crude acrylic acid.
- 140.5 mol/h of residual gas are recycled to the propene oxidation and 107.7 mol/h of residual gas are incinerated.

The space-time yield of crude acrylic acid in the traditional parallel arrangement corresponds to that in Example A) according to the invention. In contrast to the procedure according to the invention, however, the traditional parallel arrangement requires the recycling of 140.5 mol/h of recycle gas in order to operate the gas-phase partial oxidation safely outside the explosion range from the outset.

We claim:

1. A process for the preparation of acrolein by gas-phase partial oxidation of propene with molecular oxygen under heterogeneous catalysis over solid-state catalysts, wherein a reaction gas starting mixture which contains propene and molecular oxygen in a molar $C_3H_6:O_2$ ratio of >1 is first passed, at elevated temperatures, through a first reaction zone I equipped with a first solid-state catalyst load I and a portion of the propene contained in the reaction gas starting mixture is oxidized to acrolein and then, to complete the partial oxidation of the propene to acrolein, the product gas mixture I emerging from the reaction zone I is passed, at elevated temperatures, through at least one further reaction zone having a solid catalyst load and, in at least one of the one or more further reaction zones, the molar ratio, present in the reaction gas mixture, of molecular oxygen to propene is increased by metering in molecular oxygen and/or a gas containing molecular oxygen, with the proviso that, in the product gas mixture emerging from the last reaction zone, at least 90 mol %, based on the propene fed to the reaction zone I, of the propene are converted with a selectivity of the acrolein formation of ≧80 mol %.

2. A process as claimed in claim 1, wherein, in the product gas mixture emerging from the final reaction zone, at least 95 mol %, based on the propene fed to the reaction zone I, of the propene are converted with a selectivity of the acrolein formation of ≧85 mol %.

3. A process as claimed in claim 1, wherein the reaction gas starting mixture contains the propene and molecular oxygen in a molar $C_3H_6:O_2$ ratio of from ≧1.1 to ≦3.

4. A process as claimed in claim 1, wherein the total number of reaction zones is two.

5. A process as claimed in claim 4, wherein the propene conversion in the first reaction zone is from 20 to 60 mol %, based on the propene fed in.

6. A process as claimed in claim 1, wherein the total amount of molecular oxygen required in the course of the process is fed in as a component of air.

7. A process as claimed in claim 1, wherein the molar ratio of molecular oxygen to propene is >1 at least in the reaction gas mixture fed to the final reaction zone.

8. A process as claimed in claim 1, which is carried out continuously without a component of the reaction gas mixture being circulated.

9. A process for the preparation of acrylic acid from propene, which comprises preparing acrolein by the process as claimed in claim 1, and converting the acrolein to acrylic acid.

* * * * *